United States Patent
Shibib et al.

(10) Patent No.: US 6,890,804 B1
(45) Date of Patent: May 10, 2005

(54) METAL-OXIDE-SEMICONDUCTOR DEVICE FORMED IN SILICON-ON-INSULATOR

(75) Inventors: Muhammed Ayman Shibib, Wyomissing, PA (US); Shuming Xu, Schnecksville, PA (US)

(73) Assignee: Agere Systems, Inc., Allentown, PA (US)

( * ) Notice: Subject to any disclaimer, the term of this patent is extended or adjusted under 35 U.S.C. 154(b) by 0 days.

(21) Appl. No.: 10/719,195

(22) Filed: Nov. 21, 2003

(51) Int. Cl.[7] .................. H01L 21/84; H01L 29/76
(52) U.S. Cl. ................ 438/163; 438/286; 257/336; 257/340
(58) Field of Search ................. 438/163, 268, 438/286, 481; 257/336, 340, 341, 344

(56) References Cited

U.S. PATENT DOCUMENTS

| | | | | |
|---|---|---|---|---|
| 5,369,045 A | * | 11/1994 | Ng et al. | 438/286 |
| 6,087,232 A | * | 7/2000 | Kim et al. | 438/286 |
| 6,258,674 B1 | * | 7/2001 | Kwon et al. | 438/286 |
| 6,297,534 B1 | * | 10/2001 | Kawaguchi et al. | 257/341 |
| 6,461,902 B1 | | 10/2002 | Xu et al. | 438/163 |
| 2002/0109184 A1 | * | 8/2002 | Hower et al. | 257/336 |

OTHER PUBLICATIONS

J. Cai et al., "A Partial SOI Technology for Single–Chip RF Power Amplifiers," IEEE, pp. 40.3.1–40.3.4, 2001.
S. Matsumoto et al., "A Quasi–SOI Power MOSFET for Radio Frequency Applications Formed by Reversed Silicon Wafer Direct Bonding," IEEE, pp. 1448–1453, 2001.

* cited by examiner

*Primary Examiner*—Chandra Chaudhari

(57) ABSTRACT

A semiconductor device includes a substrate of a first conductivity type, an insulating layer formed on at least a portion of the substrate, and an epitaxial layer of a second conductivity type formed on at least a portion of the insulating layer. First and second source/drain regions of the second conductivity type are formed in the epitaxial layer proximate an upper surface of the epitaxial layer, the first and second source/drain regions being spaced laterally from one another. A gate is formed above the epitaxial layer proximate the upper surface of the epitaxial layer and at least partially between the first and second source/drain regions. The device further includes a first source/drain contact formed through the epitaxial layer and insulating layer, the first source/drain contact configured so as to be in direct electrical connection with the substrate, the first source/drain region and the epitaxial layer, and a second source/drain contact formed through the epitaxial layer, the second source/drain contact configured so as to be in direct electrical connection with the second source/drain region.

21 Claims, 3 Drawing Sheets

METAL-OXIDE-SEMICONDUCTOR DEVICE FORMED IN SILICON-ON-INSULATOR

FIELD OF THE INVENTION

The present invention relates generally to metal-oxide-semiconductor (MOS) devices, and more particularly relates to techniques for fabricating an improved MOS device in silicon-on-insulator (SOI).

BACKGROUND OF THE INVENTION

Power MOS devices, including lateral diffused MOS (LDMOS) devices, are generally difficult to manufacture in SOI, although the benefits of using an SOI process to enhance the high-frequency performance of discrete or integrated LDMOS devices, particularly in a radio frequency (RF) range of operation (e.g., above one gigahertz), are known.

In an article by J. Cai et al., "A Partial SOI Technology for Single-Chip RF Power Amplifiers," IEEE IEDM, pp. 40.3.1–40.3.4, 2001, a process is described for building an RF LDMOS device in partial SOI by employing multiple trench and dielectric etching to form thin "walls" of silicon, and then oxidizing these walls to form one layer of SOI under the drain region of the RF LDMOS device and away from the channel region. This methodology, however, undesirably forces a significant portion of the lightly-doped drain (LDD) region of the device to be in contact with the p-type substrate, and thus does not allow the on-resistance of the device to be reduced by increasing the doping of the LDD region. Furthermore, fabricating the RF LDMOS device using the partial SOI process is difficult to manufacture and is therefore costly.

In another article, authored by S. Matsumoto et al., "A Quasi-SOI Power MOSFET for Radio Frequency Applications Formed by Reversed Silicon Wafer Direct Bonding," IEEE Transactions on Electron Devices, Vol. 48, No. 7, pp. 1448–1453, July 2001, a process is described in which after an LDMOS device is fabricated but before metalization, a thick oxide layer is deposited on the device wafer and a second wafer is bonded to the device wafer. The device wafer is then inverted and thinned substantially so that only the top region remains. More processing is then done to build the dielectric oxide on top of the active portion of the device, and then metalization is added. The source, drain and gate terminals are brought out only from an upper surface of the device wafer. In an RF LDMOS device formed using this process, the doping in the LDD region significantly affects the breakdown voltage, and thus the doping concentration of the LDD region cannot generally be increased without also reducing the breakdown voltage. Therefore, like in the previously described methodology, the on-resistance generally cannot be reduced in an LDMOS device formed using this process. Moreover, the fabrication process is difficult and costly to implement.

There exists a need, therefore, for techniques for forming an MOS device capable of improved performance and reliability that does not suffer from one or more of the above-noted deficiencies associated with conventional MOS devices.

SUMMARY OF THE INVENTION

In accordance with one aspect of the invention, an MOS device includes a semiconductor substrate of a first conductivity type, an insulating layer formed on at least a portion of the substrate, and an epitaxial layer of a second conductivity type formed on at least a portion of the insulating layer. First and second source/drain regions of the second conductivity type are formed in the epitaxial layer proximate an upper surface of the epitaxial layer, the first and second source/drain regions being spaced laterally from one another. A gate is formed above the epitaxial layer proximate the upper surface of the epitaxial layer and at least partially between the first and second source/drain regions. The device further includes a first source/drain contact formed through the epitaxial layer and insulating layer, the first source/drain contact configured so as to be in direct electrical connection with the substrate, the first source/drain region and the epitaxial layer, and a second source/drain contact formed through the epitaxial layer, the second source/drain contact configured so as to be in direct electrical connection with the second source/drain region.

The present invention provides techniques for forming a semiconductor device having enhanced performance and reliability, particularly in a high frequency range of operation (e.g., above about one gigahertz). The unique semiconductor arrangement allows an on-resistance of the device to be substantially reduced without significantly reducing the breakdown voltage. Additionally, this arrangement beneficially prevents triggering of a parasitic bipolar transistor associated with the MOS device. The techniques of the present invention can be advantageously employed to fabricate an integrated circuit (IC) device, for example, an LDMOS device, using conventional semiconductor fabrication process technology, such as, but not limited to, CMOS, bipolar, etc. Consequently, the cost of manufacturing the IC device is not significantly increased.

These and other features and advantages of the present invention will become apparent from the following detailed description of illustrative embodiments thereof, which is to be read in connection with the accompanying drawings.

DETAILED DESCRIPTION OF THE INVENTION

The present invention will be described herein in the context of an illustrative MOS integrated circuit fabrication technology suitable for forming discrete RF LDMOS transistors, as well as other devices and/or circuits. It should be appreciated, however, that the present invention is not limited to the fabrication of this or any particular device or circuit. Rather, the invention is more generally applicable to techniques for forming a semiconductor device in partial SOI having improved performance and reliability.

Although implementations of the present invention are described herein with specific reference to an LDMOS device and a complementary metal-oxide-semiconductor (CMOS) fabrication process, it is to be appreciated that the techniques of the present invention are similarly applicable to other fabrication processes (e.g., bipolar) and/or the formation of other devices, such as, but not limited to, an MOS field-effect transistor (MOSFET), a bipolar junction transistor (BJT), a vertical diffused MOS (DMOS) device, an extended drain MOSFET device, etc., with or without modifications thereto, as will be understood by those skilled in the art. Furthermore, although the invention will be described herein in the context of an n-channel MOS device, it is well understood by those skilled in the art that a p-channel MOS device could be formed by simply substituting opposite polarities to those given for the n-channel embodiment, and that the techniques and advantages of the present invention will similarly apply to the alternative embodiment.

It is to be understood that the various layers and/or regions shown in the accompanying figures may not be drawn to scale, and that one or more semiconductor layers and/or regions of a type commonly used in such integrated circuit structures may not be explicitly shown in a given figure for ease of explanation. This does not imply that the semiconductor layer(s) and/or region(s) not explicitly shown are omitted in the actual integrated circuit structure.

Figure 1:
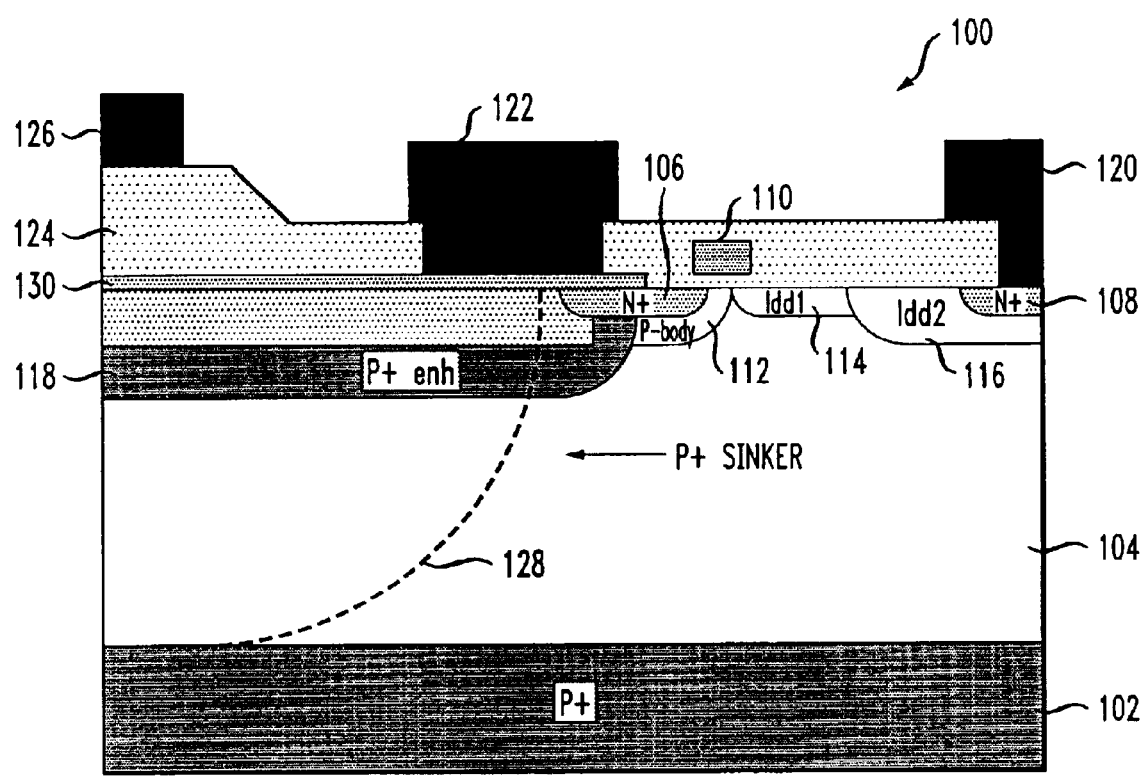
FIG. 1 is a cross-sectional view illustrating at least a portion of an LDMOS device in which the techniques of the present invention may be implemented.

FIG. 1 illustrates a cross-sectional view of at least a portion of a semiconductor wafer 100 that can be modified to implement the techniques of the present invention. The wafer 100 includes an LDMOS device formed on a substrate 102. The LDMOS device includes a source region 106 and a drain region 108 formed in an epitaxial layer 104 of the wafer 100. The LDMOS device further includes a gate 110 formed above a body region (P-body) 112 of the device. The body region 112 is at least partially formed between the source and drain regions. An n-type drift region is generally formed in the epitaxial layer 104 of the LDMOS device which may comprise a first LDD region (Idd1) 114 and a second LDD region (Idd2) 116 formed between the body region 112 and drain region 108. The source region 106 in the LDMOS device may include a p-type enhancement region 118 formed in the epitaxial layer 104 adjacent to the source region 106 and extending laterally opposite the body region 112. The enhancement region 118 may be electrically connected to the source region 106 by a conductive layer 130, which may comprise, for example, a silicide. An oxide layer 124 is generally formed on an upper surface of the wafer 100 to electrically isolate the source, drain and gate areas of the device as well as to protect the device.

The LDMOS device further includes a drain contact 120 and a source contact 122, each of which may be formed through the oxide layer 124 and electrically connected to the drain region 108 and source region 106, respectively. Electrical connection to the source region 106 may also be made from a bottom surface of the substrate 102 via one or more trench sinkers 128 formed through the epitaxial layer 104 which provide a low-resistance (e.g., less than about 8 ohms per square) electrical path between the source region 106 and the substrate 102. A gate contact 126 is also included for providing an electrical connection to the gate 110.

In many applications, for example, power applications and applications in which high-frequency operation is desired, such as in a radio frequency (RF) range (e.g., above 1 gigahertz (GHz)), it is desirable to minimize the on-resistance, $R_{DS}$, associated with the MOS device. In an LDMOS device, since the on-resistance is dominated primarily by the characteristics of the LDD region, one known methodology for reducing the on-resistance is to increase the doping concentration of the LDD region. However, increasing the doping concentration of the LDD region also undesirably reduces the breakdown voltage of the device and increases hot carrier degradation in the device. In order to allow the on-resistance of the LDMOS device to be reduced without significantly reducing the breakdown voltage of the device, a unique partial SOI semiconductor structure is proposed, which will be described in detail herein below.

Figure 2:
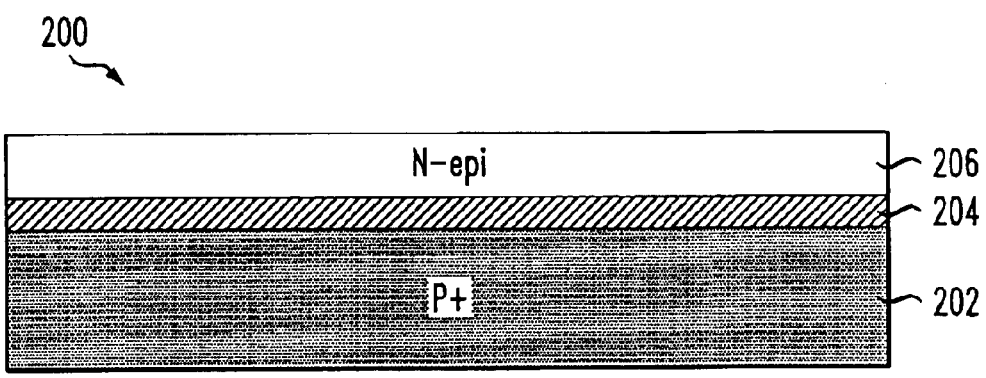
FIG. 2 is a cross-sectional view illustrating at least a portion of an SOI wafer structure in which the techniques of the present invention are implemented.

FIG. 2 illustrates a cross-sectional view of at least a portion of a semiconductor wafer 200 in which the techniques of the present invention are implemented. The wafer 200 comprises a substrate 202 which is commonly formed of single-crystal silicon (e.g., having a <100> or <111> crystal orientation), although suitable alternative materials may also be used, such as, but not limited to, germanium (Ge), gallium arsenide (GaAs), etc. Additionally, the substrate is preferably modified by adding an impurity or dopant to change the conductivity of the material (e.g., n-type or p-type). In a preferred embodiment of the invention, the substrate 202 is of p-type conductivity and may thus be referred to as a p+ substrate. A p+ substrate may be formed by adding a p-type impurity or dopant (e.g., boron) of a desired concentration (e.g., about $5 \times 10^{18}$ to about $5 \times 10^{19}$ atoms per cubic centimeter) to the substrate material, such as by a diffusion or implant step, to change the conductivity of the material as desired.

The wafer 200 further includes an insulating layer 204 formed on at least a portion of the substrate 202. The insulating layer 204 may comprise, for example, an oxide (e.g., silicon dioxide), nitride (e.g., silicon nitride), or an alternative insulating material. Insulating layer 204 may be formed of a desired thickness (e.g., about 0.4 micron to about 2 microns) using, for example, a conventional oxide growth or deposition process, although alternative methodologies for forming the insulating layer may be employed, as will be known by those skilled in the art. An epitaxial layer 206 is preferably formed on at least a portion of the insulating layer 204. By introducing selected types of impurities (e.g., boron, phosphorous, arsenic, etc.) into the epitaxial layer 206, a resistivity of the epitaxial layer can be modified as desired. The thickness of the epitaxial layer is typically about 4 to 6 micrometers, although the present invention is not limited to any particular thickness of the epitaxial layer. Because the epitaxial layer 206 typically comprises silicon, the arrangement of the wafer 200 may be referred to as an SOI structure.

In a preferred embodiment of the invention, the epitaxial layer 206 is doped with an n-type impurity (e.g., arsenic or phosphorus). The doping concentration of the epitaxial layer 206 is preferably significantly higher (e.g., about $2 \times 10^{16}$ to about $2 \times 10^{17}$ atoms per cubic centimeter) in comparison to the doping concentration of a conventional epitaxial layer or LDD region, which is typically about $10^{16}$ to about $10^{17}$ atoms per cubic centimeter. The doping concentration of the epitaxial layer 206 can thus be substantially matched to the doping concentration of a traditional LDD region. By substantially increasing the doping concentration of the epitaxial layer 206 in this manner, the epitaxial layer can serve as the LDD region for the LDMOS device, thereby eliminating the need for an additional LDD implant and drive-in step.

In an alternative embodiment of the invention, the SOI structure may be formed using a wafer bonding process. As will be understood by those skilled in the art, the wafer bonding process typically involves providing a first wafer comprising a p-type substrate and a second wafer comprising an n-type substrate. An insulating layer, preferably comprising an oxide or nitride (e.g., silicon dioxide or silicon nitride), is subsequently formed (e.g., grown or deposited) on an upper surface of the first and/or second wafers. It is to be appreciated that the insulating layer need only be formed on one of the wafers, although each wafer may include the insulating layer. The second wafer is then inverted so that the two wafers are joined together at their respective insulating layers, such that the p-type substrate of the first wafer forms the substrate 202 and the n-type substrate of the second wafer forms the epitaxial layer 206 of the SOI structure depicted in FIG. 2.

If the epitaxial layer is formed relatively thin (e.g., about 0.5 micron), the insulating layer 204 may be formed as a buried insulating layer, such as, for example, by using a separation by implantation of oxygen (SIMOX) process. During the SIMOX process, rather than forming the insulating layer 204 on the substrate 202 and forming the epitaxial layer on the insulating layer, the epitaxial layer 206 is formed directly on at least a portion of the substrate 202, such as by using a conventional epitaxy process. Then, oxygen or nitrogen ions are implanted through the epitaxial layer 206 to form a layer within the silicon wafer. A high temperature furnace (e.g., at a temperature of about 1000 degrees Celsius) completes the formation of the buried insulating layer 204 (e.g., comprising silicon dioxide or silicon nitride, respectively) to form the SOI wafer structure shown in FIG. 2.

The term "wafer" is often used interchangeably with the term "silicon body," since silicon is typically employed as the semiconductor material comprising the wafer. It should be appreciated that although the present invention is illustrated herein using a portion of a semiconductor wafer, the term "wafer" may include a multiple-die wafer, a single-die wafer, or any other arrangement of semiconductor material on which a semiconductor structure may be formed.

Figure 3:
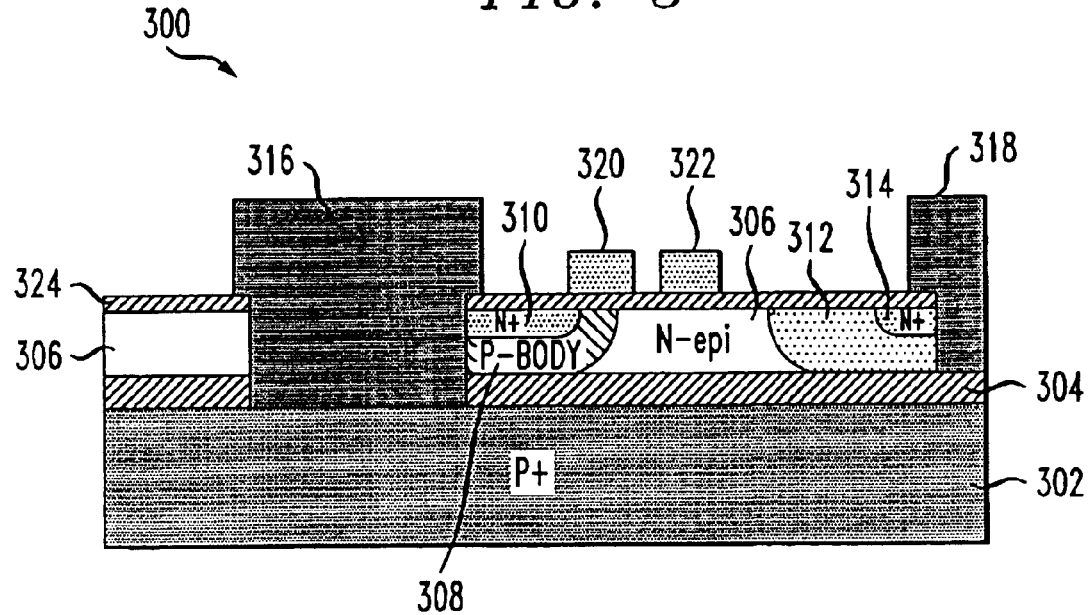
FIG. 3 is a cross-sectional view depicting at least a portion of an exemplary LDMOS device, formed in accordance with an illustrative embodiment of the present invention.

FIG. 3 depicts at least a portion of an exemplary LDMOS device formed on an SOI wafer 300, in accordance with an illustrative embodiment of the invention. The SOI wafer 300 may be formed in a manner consistent with the formation of the SOI wafer 200 previously described in connection with FIG. 2, although alternative SOI structures may be similarly employed. Specifically, the wafer 300 preferably comprises a substrate 302 which may be formed, for example, by heavily doping single-crystal silicon with a p-type impurity or dopant (e.g., boron) of a desired concentration (e.g., about $5 \times 10^{18}$ to about $5 \times 10^{19}$ atoms per cubic centimeter). A first insulating layer 304, which may comprise, for example, an oxide (e.g., silicon dioxide), is formed on at least a portion of the substrate 302. An epitaxial layer 306 having a conductivity type opposite the conductivity type of the substrate 302 is formed on at least a portion of the first insulating layer 304. In a preferred embodiment of the invention, the epitaxial layer 306 is doped with an n-type impurity or dopant (e.g., arsenic or phosphorus) of a desired concentration (e.g., about $10^{17}$ to about $10^{18}$ atoms per cubic centimeter).

The characteristics of the epitaxial layer 306 (e.g., thickness, doping level, etc.) can affect the current density and/or power dissipation in the device. For instance, a thickness of the epitaxial layer 306 can be adjusted to compensate for heat dissipation in the device. Thus, as the thickness of the epitaxial layer 306 is increased, the ability to dissipate heat in the device improves. Additionally, by increasing the doping concentration in the epitaxial layer 306, an on-resistance, $R_{DS}$, associated with the device can be beneficially reduced without significantly reducing the breakdown voltage of the device. Since transconductance associated with the LDMOS device is inversely proportional to the on-resistance, reducing the on-resistance of the device beneficially increases the transconductance, thereby improving the high-frequency performance of the device.

The exemplary LDMOS device further includes a source region 310 and a drain region 314 formed in the epitaxial layer 306 of the wafer 300, such as by an implant or diffusion process. The source and drain regions are preferably doped, such as by an implant process, with an impurity (e.g., boron, phosphorus, arsenic, etc.) of a known concentration level to selectively change the conductivity of the material as desired. Preferably, the source and drain regions 310, 314 have a conductivity type associated therewith which is opposite a conductivity type of the substrate 302. In a preferred embodiment of the invention, the source and drain regions 310, 314 are of n-type conductivity.

It is to be appreciated that, in the case of a simple MOS device, because the MOS device is symmetrical in nature, and thus bidirectional, the assignment of source and drain designations in the MOS device is essentially arbitrary. Therefore, the source and drain regions may be referred to generally as first and second source/drain regions, respectively, where "source/drain" in this context denotes a source region or a drain region. In an LDMOS device, which is generally not bidirectional, such source and drain designations may not be arbitrarily assigned.

A body region 308 and a drift region, which may comprise an LDD region 312, are formed proximate an upper surface of the exemplary LDMOS device, just beneath an interface between the silicon epitaxial layer 306 and a second insulating layer 324, which in a preferred embodiment is formed of an oxide (e.g., silicon dioxide ($SiO_2$), etc.), although other suitable insulating materials may be used (e.g., silicon nitride). Since the epitaxial layer 306 often comprises silicon, the interface between the epitaxial layer 306 and the second insulating layer 324 may be referred to as a silicon/oxide interface. The body region 308 is formed at least partially below and adjacent to the source region 310 while the LDD region 312 extends laterally from drain region 314 toward the body region. The body region 308 may be formed of a material having the same conductivity type as the substrate, preferably p-type in the exemplary LDMOS device, and may therefore be referred to as a p-body. The LDD region may be formed of a material having the same conductivity type as the source and drain regions, preferably n-type, although the relative doping concentration of the LDD region compared to the source and drain regions is typically lower.

The exemplary LDMOS device further includes a gate 320 formed above at least a portion of the body region 308 and proximate the silicon/oxide interface of the wafer 300. The gate may comprise, for example, polysilicon material, although alternative suitable materials (e.g., metal) may be similarly employed. The gate 320 is electrically isolated from an active area of the wafer via the second insulating layer 324. Since the insulating layer under the gate 320 preferably comprises an oxide (e.g., silicon dioxide), the portion of the second insulating layer 324 under the gate 320 may be referred to herein as gate oxide.

A shielding electrode 322, which may be referred to herein as a dummy gate, is preferably formed in the exemplary LDMOS device between the gate 320 and the drain region 314. The dummy gate 322, which may comprise, for example, polysilicon, is spaced laterally from the gate 320 and is preferably substantially non-overlapping relative to the gate. Although not shown, the dummy gate 322 in the exemplary LDMOS device, when used, is preferably electrically connected (e.g., strapped) to the source region 310, such as by forming a conductive layer (e.g., aluminum, gold, etc.) between the dummy gate and the source region. Like the gate 320, the dummy gate 322 is preferably formed on the second insulating layer 324 for electrically isolating the dummy gate from an active region of the wafer 300.

The dummy gate 322 can be formed concurrently with the gate 320 in the same processing step. In this manner, the dummy gate 322 is preferably self-aligned to the gate 320. The thickness of the second insulating layer 324 (e.g., silicon dioxide) beneath the gate 320 and dummy gate 322 may be substantially the same. Thus, like the gate 320, the dummy gate 322 is preferably formed in close relative proximity (e.g., 200 nanometers (nm)) to the silicon/oxide interface of the wafer 300. It is to be appreciated, however, that the relative thicknesses of the second insulating layer 324 under the gate 320 and dummy gate 322 need not be the same. Furthermore, although the size and shape of the dummy gate 322 relative to the gate 320 may be substantially the same, the configuration of the gate and/or dummy gate are not limited to the precise size or shape shown, but may be formed in alternative configurations, as will be understood by those skilled in the art.

The dummy gate 322 beneficially reduces hot-carrier injection (HCI) effects proximate the silicon/oxide interface in the vicinity of the corners of the gate 320. A dummy gate suitable for use in conjunction with the present invention can be found, for example, in a related U.S. application Ser. No. 10/623,983 entitled "Shielding Structure for Use in a Metal-Oxide-Semiconductor Device," filed on Jul. 15, 2003, which is incorporated by reference herein. Because the dummy gate 322 is tied to substantially the same voltage potential as the substrate 302, the dummy gate and substrate effectively act as electrical shielding regions through the second insulating layer 324 and first insulating layer 304, respectively, thus exploiting a phenomena known as reduced surface field (RESURF) effect. By diffusing the drift region with an appropriate doping profile and/or adjusting a thickness of the drift region, the exemplary LDMOS device can be configured such that the reverse-biased junctions between the body region 308 and source region 310, and between the body region and the substrate 302, substantially deplete the entire drift region of charge carriers. This condition generally creates a relatively uniform electric field in the drift region which effectively maximizes the breakdown voltage associated with the device, in at least one aspect, by substantially eliminating peaks in the electric field that would otherwise initiate carrier ionization which may lead to premature avalanche breakdown. The structure of the present invention essentially doubles the effectiveness of the RESURF phenomena in the device by providing two electrical shielding regions, as previously stated. Consequently, this phenomena may be referred to herein as a double RESURF effect.

A source contact 316 and a drain contact 318 may be formed on an upper surface of the wafer 300, such as, for example, by conventional photolithographic patterning and etching, for providing an electrical connection to the source region 310 and drain region 314, respectively. The source and drain contacts may comprise a metal, such as, for example, aluminum or gold. A gate contact (not shown) may also be formed on the upper surface of the wafer 300, or in an alternative location, for providing an electrical connection to the gate 320. If a distance between the source contact 316 and the gate 320 is significant (e.g., greater than about a few micrometers), then the exemplary LDMOS device may further include an enhancement region (not shown) of a conductivity type opposite that of the source region 310 formed proximate an upper surface of the wafer 300 and extending laterally from the body region 308 in a direction opposite the drain region 314, as may be traditionally employed.

An important aspect of the present invention is the unique formation of the source contact 316. As apparent from the figure, the source contact 316 may be provided by forming a trench through the second insulating layer 324, epitaxial layer 306 and first insulating layer 304 to at least partially expose the substrate 302. The trench is then filled with a conductive material, such as, for example, gold or aluminum. The source contact 316 itself thus advantageously provides a low-resistance electrical connection between the epitaxial layer 306, the substrate 302 and the source region 310. As an added benefit, the source contact 316, by effectively shorting the epitaxial layer 306, substrate 302 and source region 310 together, prevents triggering of a parasitic npn bipolar transistor (not shown) associated with the LDMOS device. The parasitic npn transistor is formed whereby the p-type substrate 302 functions as a base of the parasitic transistor, the n-type epitaxial layer 306 functions as a collector and the n-type source 310 functions as an emitter.

Figure 4:
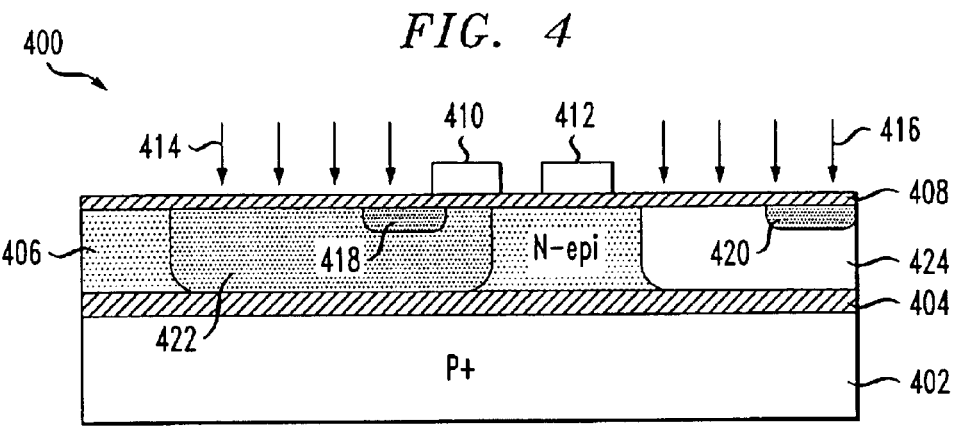
FIGS. 4–6 are cross-sectional views depicting steps in a semiconductor fabrication process which may be used in forming an exemplary MOS device, in accordance with an illustrative embodiment of the present invention.
Figure 5:
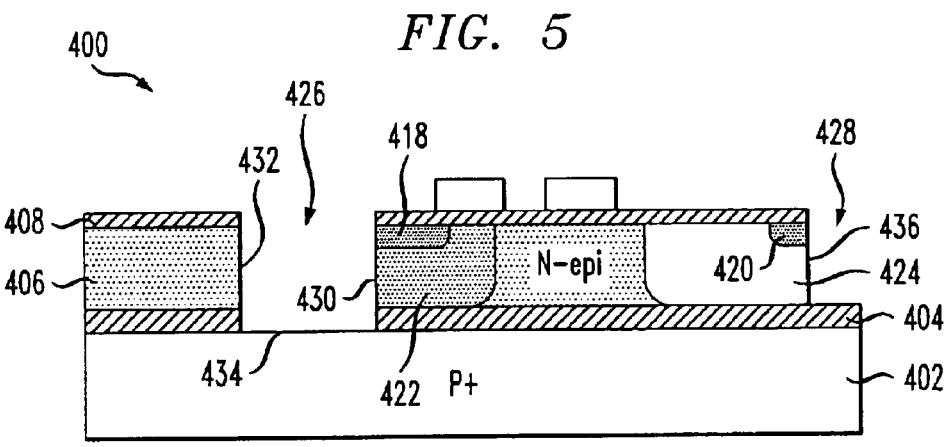
Figure 6:
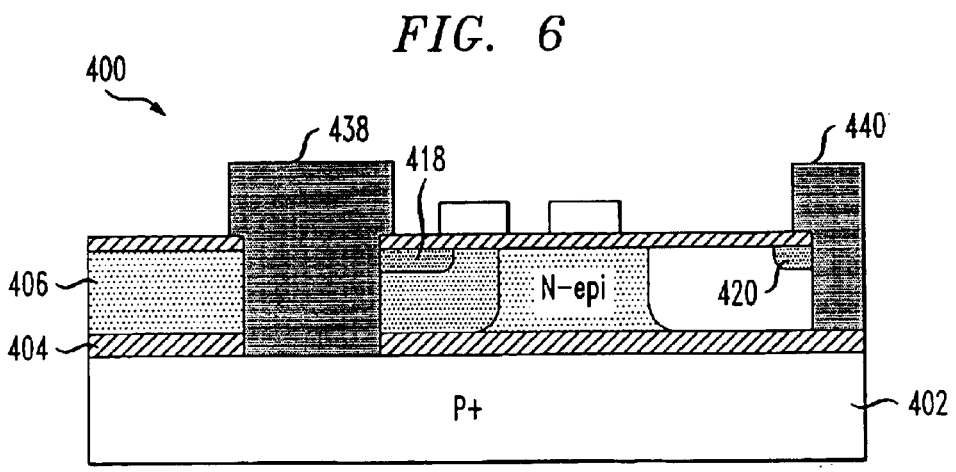

FIGS. 4–6 depict steps in an illustrative methodology which may be used in forming the exemplary LDMOS device shown in FIG. 3, in accordance with one embodiment of the present invention. The illustrative methodology will be described in the context of a conventional CMOS-compatible semiconductor fabrication process technology. It is to be understood that the invention is not limited to this or any particular methodology for fabricating the device. Furthermore, as previously stated, the various layers and/or regions shown in the figures may not be drawn to scale and certain commonly used semiconductor layers may have been omitted for ease of explanation.

FIG. 4 depicts a cross section of at least a portion of an exemplary wafer 400 in which the techniques of the present invention may be implemented. The exemplary wafer 400 utilizes an SOI structure, which may be formed in a manner consistent with the SOI structure shown in FIG. 2, that includes a substrate 402, a first insulating layer 404 formed on at least a portion of the substrate, and an epitaxial layer 406 formed on at least a portion of the first insulating layer 404. The substrate 402 is preferably a p-type substrate having a high impurity concentration (e.g., about $5 \times 10^{18}$ to about $5 \times 10^{19}$ atoms per cubic centimeter), although an n+ type substrate may alternatively be employed. The first insulating layer 404 preferably comprises an oxide (e.g., silicon dioxide) of a desired thickness (e.g., about 0.4 micrometers to about 2 micrometers for a conventional 0.35-micrometer CMOS process), although alternative insulating materials (e.g., silicon nitride) and thicknesses may be used. The epitaxial layer 406 preferably comprises n-type silicon having a significantly higher impurity doping concentration (e.g., about $2 \times 10^{16}$ to about $2 \times 10^{17}$ atoms per cubic centimeter) compared to a traditional epitaxial layer or LDD region.

A p-body region 422 may be formed in the epitaxial layer 406 such as, for example, by using a deep diffusion or implant step. During the diffusion step, a p-type impurity (e.g., boron) 414 of a known concentration level is preferably used. At least a portion of the body region 422 will form a body region of the exemplary LDMOS device. An LDD region 424 may also be formed in the epitaxial layer 406, such as, for example, by using a diffusion or implant process. During this diffusion step, an n-type impurity (e.g., phosphorous or arsenic) 416 of a known concentration level is preferably used. The LDD region 424 is formed proximate an upper surface of the wafer 400 and spaced laterally from the p-body region 422. Since the epitaxial layer 406 is more heavily doped, at least compared to a conventional LDMOS device, the need for a second LDD diffusion or implant step, as is traditionally performed, can be eliminated.

A gate 410 is formed on an upper surface of a second insulating layer 408, which may comprise an oxide (e.g., silicon dioxide). The gate 410 may be fabricated from a polycrystalline silicon (polysilicon) layer formed over the thin (e.g., about 300–400 angstroms) insulating layer 408, such as, for example, using a chemical vapor deposition (CVD) technique. The second insulating layer 408 under the gate 410 is often referred to as gate oxide. The polysilicon layer is generally patterned using, for example, a conventional photolithographic process, followed by an etching step (e.g., dry etching) to form gate 308, as will be understood by those skilled in the art. A dummy gate 412 may also be fabricated on at least a portion of the second insulating layer 408. The dummy gate 412, if used, is preferably spaced laterally from the gate 410 in a direction opposite the p-body region 422 and is non-overlapping relative to the gate. Like the gate 410, the dummy gate 412 may comprise polysilicon material.

A source region 418 is formed in the p-body region 422 and a drain region 420 is formed in the LDD region 424. The source and drain regions 418, 420 may be formed, for example, by diffusing or implanting an n-type impurity (e.g., arsenic or phosphorous) of a known concentration level into respective regions 422, 424 of the device. The source region 418 preferably uses a peripheral end of the gate 410 to at least partially define the source region, and thus the source region may be considered to be self-aligned with the gate.

FIG. 5 illustrates the formation of at least one source contact opening 426 through the second insulating layer 408, source region 418, epitaxial layer 406 and first insulating layer 404, to at least partially expose the substrate 402. Likewise, at least one drain contact opening 428 is formed through the LDD region 424, drain region 420, and epitaxial layer 406, stopping at the first insulating layer 404. The contact openings 426, 428 may be formed as shallow trenches by selectively patterning the second insulating layer 408, for example, using a conventional photolithographic process, followed by an etching step.

During the photolithographic patterning process, a layer of photoresist (not shown) is first deposited on the upper surface of the wafer 400 to prevent the second insulating layer 408 from being removed in a subsequent etching process. The photoresist is then exposed to light (e.g., ultra violet) in a manner which allows the photoresist to be removed in areas of the wafer in which the opening 426 is to be formed. During the etching process, which may comprise, for example, an anisotropic dry etch, the first insulating layer 404 is preferably used as an etch stop. It is to be understood that alternative etching techniques may be similarly employed for forming the contact openings, such as, but not limited to, reactive ion etching (RIE), wet etching, etc. The opening 426 in the source region is then exposed by photoresist and the oxide at the bottom of the opening forming the first insulating layer 404 is removed, thereby exposing the substrate 402. It is to be appreciated that the contact openings 426, 428 may be formed using an alternative methodology, such as, for example, a conventional v-groove process.

Any organic material remaining on one or more side walls and bottom wall of the trenches 426, 428 are preferably removed, such as by using an etching process (e.g., dry or wet etching). In this manner, the epitaxial layer 406 will be exposed through at least a portion of sidewall 432 of the trench 426. Likewise, the source region 418 and substrate 402 will be at least partially exposed through sidewall 430 and bottom wall 434, respectively, of the trench 426. The drain region 420 is at least partially exposed through a sidewall 436 of trench 428.

FIG. 6 illustrates an exemplary methodology for forming source and drain contacts of the LDMOS device. Although not shown, a silicide layer is preferably formed on the sidewalls and bottom wall of each of the trenches, so as to substantially line the trenches. The silicide layer may be formed, for example, using a deposition process (e.g., CVD), although alternative techniques may be used, as will be known by those skilled in the art. With regard to the source contact opening, the silicide layer facilitates a low-resistance electrical connection between the substrate 402, epitaxial layer 406 and source region 418, which are generally comprised of silicon, and a conductive material 438 deposited in the source contact opening 426 shown in FIG. 5. Likewise, with regard to the drain contact opening, the silicide layer facilitates a low-resistance electrical connection between the drain region 420 and a conductive material 440 deposited in the drain contact opening 428 shown in FIG. 5. The characteristics of the silicide layer make it able to form a bond with the silicon and with the conductive material, which may be a metal (e.g., gold, aluminum, etc.). The conductive material 438, 440 is deposited in the corresponding contact opening so as to substantially fill the opening, thereby forming the source and drain contacts, respectively.

As previously explained, an important aspect of the present invention is that the source contact 438 provides a local low-resistance electrical connection between the substrate 402, the source region 418 and the epitaxial layer 406, effectively preventing the triggering of the parasitic bipolar npn transistor created by the p-n junctions between the p-substrate 402 and n-epitaxial layer 406, and between the p-substrate and n-source region 418. Moreover, this local connection is made through the first insulating layer 404 without substantially disrupting the continuity of the first insulating layer proximate the drain and source regions. Consequently, since substantially no portion of the epitaxial layer 406 proximate the drain region 420 is in direct contact with the substrate 402, at least the portion of the epitaxial layer proximate the drain region can be more heavily doped, thereby eliminating the need for an additional LDD region and the corresponding process steps required to formed such additional LDD region.

Using the techniques described herein for forming a semiconductor device in partial SOI, the on-resistance of the device can be advantageously reduced without significantly reducing the breakdown voltage associated with the device, and without significantly increasing the cost of manufacturing the device. Additional advantages of the present invention include, but are not limited to, enabling easier integration of the device with other active and/or passive components to implement, for example, an integrated RF amplifier, significantly reducing the drain-to-source (output) capacitance of the device, reducing drain leakage current, especially at high temperatures (e.g., above about 200 degrees Celsius), reducing source parasitics, especially source resistance, and improving a linearity of the device by reducing the voltage dependence of the drain-to-source output capacitance. Both the value and voltage dependence of the output capacitance may be reduced significantly using the methodologies of the invention set forth herein, thereby improving a high-frequency performance, linearity, and/or efficiency of the device.

Although illustrative embodiments of the present invention have been described herein with reference to the accompanying drawings, it is to be understood that the invention is not limited to those precise embodiments, and that various other changes and modifications may be made therein by one skilled in the art without departing from the scope of the appended claims.

What is claimed is:

1. A semiconductor device, comprising:
    a substrate of a first conductivity type;
    a first insulating layer formed on at least a portion of the substrate;
    an epitaxial layer of a second conductivity type formed on at least a portion of the first insulating layer;
    first and second source/drain regions of the second conductivity type formed in the epitaxial layer proximate an upper surface of the epitaxial layer, the first and second source/drain regions being spaced laterally from one another;
    a gate formed above the epitaxial layer proximate the upper surface of the epitaxial layer and at least partially between the first and second source/drain regions;
    a first source/drain contact formed through the epitaxial layer and first insulating layer, the first source/drain contact configured so as to be in direct electrical connection with the substrate, the first source/drain region and the epitaxial layer; and
    a second source/drain contact formed at least partially through the epitaxial layer, the second source/drain contact configured so as to be in direct electrical connection with the second source/drain region.

2. The device of claim 1, wherein the first source/drain contact is configured so as to prevent triggering of a parasitic bipolar transistor associated with the device, the parasitic bipolar transistor including a base-emitter region formed between the substrate and the first source/drain region, and a base-collector region formed between the substrate and the epitaxial layer.

3. The device of claim 2, wherein the first source/drain contact prevents triggering of the parasitic bipolar transistor by substantially shorting the epitaxial layer, the substrate and the first source/drain region together.

4. The device of claim 1, further comprising a shielding structure formed proximate the upper surface of the epitaxial layer and between the gate and the second source/drain region, the shielding structure being electrically connected to the first source/drain region, the shielding structure being spaced laterally from the gate and being substantially non-overlapping relative to the gate.

5. The device of claim 4, wherein the shielding structure is formed substantially concurrently with the gate.

6. The device of claim 4, further comprising a second insulating formed under at least a portion of the gate and the shielding structure.

7. The device of claim 6, wherein the second insulating layer formed under the gate and the shielding structure are of different thicknesses relative to one another.

8. The device of claim 1, wherein the device comprises a diffused MOS (DMOS) device.

9. The device of claim 1, wherein the device comprises a laterally diffused MOS (LDMOS) device.

10. The device of claim 1, wherein the first source/drain region comprises a source of the device and the second source/drain region comprises a drain of the device.

11. The device of claim 1, wherein the epitaxial layer is doped with an impurity having a concentration in a range of about $2 \times 10^{16}$ to about $2 \times 10^{17}$ atoms per cubic centimeter.

12. The device of claim 1, wherein the first conductivity type is p-type and the second conductivity type is n-type.

13. The device of claim 1, wherein the substrate, first insulating layer and epitaxial layer are formed by a wafer bonding process, whereby a first semiconductor wafer is provided comprising a substrate of the first conductivity type and a second semiconductor wafer is provided comprising a substrate of the second conductivity type, at least one of the first and second semiconductor wafers further comprising at least a portion of the first insulating layer formed on the respective substrates, the second semiconductor being inverted and joined to the first semiconductor wafer at the first insulating layer.

14. A method of forming a metal-oxide-semiconductor device in a semiconductor wafer, the method comprising the steps of:
    forming a first insulating layer on at least a portion of a semiconductor substrate of a first conductivity type;
    forming an epitaxial layer of a second conductivity type on at least a portion of the first insulating layer;
    forming a gate on an upper surface of the semiconductor wafer;
    forming a body region of the first conductivity type in the epitaxial layer proximate the upper surface of the epitaxial layer, the body region being formed at least partially under the gate;
    forming first and second source/drain regions of the second conductivity type in the epitaxial layer, the gate being formed above and at least partially between the first and second source/drain regions;
    forming a first source/drain contact through the epitaxial layer and first insulating layer, the first source/drain contact being configured such that the first source/drain contact is in direct electrical connection with the substrate, the first source/drain region and the epitaxial layer; and
    forming a second source/drain contact at least partially through the epitaxial layer, the second source/drain contact being configured such that the second source/drain contact is in direct electrical connection with the second source/drain region.

15. The method of claim 14, further comprising the step of forming a shielding structure proximate the upper surface of the epitaxial layer and between the gate and the second source/drain region, the shielding structure being electrically connected to the first source/drain region, the shielding structure being spaced laterally from the gate and being substantially non-overlapping relative to the gate.

16. The method of claim 15, further comprising the step of forming a second insulating layer under at least a portion of the gate and the shielding structure.

17. The method of claim 16, wherein the second insulating layer formed under the gate and the shielding structure are of different thicknesses relative to one another.

18. The method of claim 14, wherein the step of forming the first source/drain contact comprises the steps of:
    forming a first trench through the epitaxial layer and first source/drain region to at least partially expose the first insulating layer;
    removing the first insulating layer proximate a bottom wall of the first trench to at least partially expose the substrate; and
    substantially filling the first trench with an electrically conductive material.

19. An integrated circuit including at least one semiconductor device, the at least one semiconductor device comprising:

a substrate of a first conductivity type;

a first insulating layer formed on at least a portion of the substrate;

an epitaxial layer of a second conductivity type formed on at least a portion of the first insulating layer;

first and second source/drain regions of the second conductivity type formed in the epitaxial layer proximate an upper surface of the epitaxial layer, the first and second source/drain regions being spaced laterally from one another;

a gate formed above the epitaxial layer proximate the upper surface of the epitaxial layer and at least partially between the first and second source/drain regions;

a first source/drain contact formed through the epitaxial layer and first insulating layer, the first source/drain contact configured so as to be in direct electrical connection with the substrate, the first source/drain region and the epitaxial layer; and a second source/drain contact formed at least partially through the epitaxial layer, the second source/drain contact configured so as to be in direct electrical connection with the second source/drain region.

20. The integrated circuit of claim 19, wherein the first source/drain contact is configured so as to prevent triggering of a parasitic bipolar transistor associated with the device, the parasitic bipolar transistor including a base-emitter region formed between the substrate and the first source/drain region, and a base-collector region formed between the substrate and the epitaxial layer.

21. The integrated circuit of claim 19, further comprising a shielding structure formed proximate the upper surface of the epitaxial layer and between the gate and the second source/drain region, the shielding structure being electrically connected to the first source/drain region, the shielding structure being spaced laterally from the gate and being substantially non-overlapping relative to the gate.

* * * * *